(12) United States Patent
Urman et al.

(10) Patent No.: US 8,391,947 B2
(45) Date of Patent: Mar. 5, 2013

(54) CATHETER WITH SHEET ARRAY OF ELECTRODES

(75) Inventors: Roy Urman, Karkur (IL); Liron Shmuel Mizrahi, Kiryat Haim (IL); Ronen Krupnik, Carmiel (IL)

(73) Assignee: Biosense Webster (Israel), Ltd., Yokneam (IL)

( * ) Notice: Subject to any disclaimer, the term of this patent is extended or adjusted under 35 U.S.C. 154(b) by 16 days.

(21) Appl. No.: 12/982,141

(22) Filed: Dec. 30, 2010

(65) Prior Publication Data

US 2012/0172697 A1   Jul. 5, 2012

(51) Int. Cl.
  *A61B 5/042* (2006.01)
  *A61B 18/14* (2006.01)
(52) U.S. Cl. .......................... 600/374; 606/41
(58) Field of Classification Search .................. 600/374; 606/41
  See application file for complete search history.

(56) References Cited

U.S. PATENT DOCUMENTS

| | | | |
|---|---|---|---|
| 4,628,937 A * | 12/1986 | Hess et al. ............... | 600/374 |
| 4,882,245 A | 11/1989 | Gelorme | |
| 5,391,199 A | 2/1995 | Ben-Haim | |
| 5,443,489 A | 8/1995 | Ben-Haim | |
| 5,480,422 A | 1/1996 | Ben-Haim | |
| 5,546,951 A | 8/1996 | Ben-Haim | |
| 5,549,108 A * | 8/1996 | Edwards et al. ............ | 600/381 |
| 5,558,091 A | 9/1996 | Acker | |
| 5,568,809 A | 10/1996 | Ben-Haim | |
| 5,846,196 A * | 12/1998 | Siekmeyer et al. ........... | 600/374 |
| 6,024,739 A | 2/2000 | Ponzi | |
| 6,064,905 A | 5/2000 | Webster, Jr. | |
| 6,068,629 A * | 5/2000 | Haissaguerre et al. ......... | 606/41 |
| 6,212,426 B1 | 4/2001 | Swanson | |
| 6,961,602 B2 * | 11/2005 | Fuimaono et al. ............ | 600/374 |
| 6,992,477 B2 | 1/2006 | Govari | |
| 7,438,714 B2 * | 10/2008 | Phan ............... | 606/49 |
| 7,991,475 B1 * | 8/2011 | Tang et al. ........... | 607/45 |
| 2006/0100618 A1 | 5/2006 | Chan | |
| 2006/0241473 A1 | 10/2006 | Kuniyasu | |
| 2008/0125772 A1 | 5/2008 | Stone | |
| 2009/0240249 A1 | 9/2009 | Chan | |
| 2011/0034912 A1 * | 2/2011 | de Graff et al. ............... | 606/21 |

FOREIGN PATENT DOCUMENTS

| | | |
|---|---|---|
| EP | 0856291 A2 | 8/1998 |
| EP | 0856291 B1 | 6/2006 |
| WO | WO 95/02995 A1 | 2/1995 |
| WO | WO 95/05768 A1 | 3/1995 |
| WO | WO 97/24983 A2 | 7/1997 |
| WO | WO 98/29033 A1 | 7/1998 |

OTHER PUBLICATIONS

European Search Report Appln No. 11196081.1-2319 / 2471446 dated Jun. 13, 2012.

* cited by examiner

*Primary Examiner* — Lee S Cohen
(74) *Attorney, Agent, or Firm* — William A. Schoneman (57) ABSTRACT

A medical device has a flexible elongated body, a handle connected to the elongated body, at least one spine connected to the elongated body, and a flexible sheet attached to the at least one spine. The flexible sheet has a plurality of electrodes thereon, wherein the flexible sheet and the plurality of electrodes define a mapping assembly for mapping electrical information in tissue, and wherein the at least one spine and the flexible sheet is movable from a collapsed configuration to a deployed configuration.

22 Claims, 5 Drawing Sheets

CATHETER WITH SHEET ARRAY OF ELECTRODES

FIELD OF THE INVENTION

The present invention relates generally to invasive medical devices capable of diagnosis and treatment within a patient's body, such as a catheter that is applied to the body of a patient, and more specifically to a medical device such as a catheter having a flexible sheet array of electrodes that is adaptable to varying surfaces of organs within a patient's body, for example, for operating within the chambers of the heart or at or within one of the many vessels associated with the heart for diagnosing and treating electrical abnormalities of the heart and/or other organs or vessels of the patient's body. It is important to note that the present invention is directed to a medical device that is particularly useful for any type of medical application requiring diagnosis and/or treatment of tissue or biological function requiring electrical signal processing.

BACKGROUND OF THE INVENTION

Electrophysiology catheters are commonly used for mapping electrical activity in a heart. Electrophysiology is a specialty within the field of cardiology for diagnosis and treatment of electrical abnormalities of the heart. By mapping the electrical activity in the heart, ectopic sites of electrical activation or other electrical activation pathways that contribute to heart malfunctions may be detected. This type of information may then allow a cardiologist to intervene and destroy the malfunctioning heart tissues. Such destruction of heart tissue is referred to as ablation, which is a rapidly growing field within electrophysiology and obviates the need for maximally invasive open heart surgery.

Attached to the electrophysiology catheters are electrodes, which are used to map, or collect electrical information about, the electrical activity in the heart. It is also known to incorporate into certain electrophysiology catheters a location or position sensor for determining the location of the electrodes being used to map the electrical activity in the heart. Such catheters are generally inserted percutaneously and fed through one or more major blood vessels into a chamber of the heart. A location sensor in the catheter, typically near the catheter's distal end, produces signals that are used to determine the position of the device relative to a frame of reference, such as a position external to the body or within the heart itself. The location sensor may be active or passive and may operate by generating or receiving electrical, magnetic or ultrasonic energy fields or other suitable forms of energy known in the art.

U.S. Pat. No. 5,391,199, the disclosure of which is incorporated herein by reference, describes a position-responsive catheter comprising miniature sensor coils (position sensor) contained in the catheter's distal end. The coils generate electrical signals in response to externally-applied magnetic fields, which are produced by field-generator coils placed outside the patient's body. The electrical signals are analyzed to determine the three-dimensional axis coordinates and three-dimensional orientations (yaw, pitch and roll) of the position sensor and distal end of the catheter.

International Publication No. WO 96/05768, the disclosure of which is also incorporated herein by reference, describes a position-responsive catheter comprising a plurality of miniature, preferably non-concentric, sensor coils fixed in the catheter's distal end. As in U.S. Pat. No. 5,391,199, electrical signals generated by these coils in response to an externally-applied magnetic field are analyzed so as to determine, for example, the six-dimensional coordinates of these coils, i.e. the position coordinates and the orientation coordinates.

Catheters and systems utilizing such technical features and functionality described above include the NAVISTAR™ diagnostic and ablation catheter and the PENTARAY™ high density mapping catheter as example devices used in conjunction with the CARTO® mapping and navigation system manufactured and sold by Biosense Webster, Inc.

Multiple position-sensing devices may be placed in a known, mutually-fixed spatial relation at or adjacent to the distal end of a catheter, as described, for example, in International Publication No. WO 97/24983, the disclosure of which is incorporated herein by reference. This publication describes a catheter having a substantially rigid structure at its distal end, to which one or more position sensors are fixed. The sensors are used to determine the position and orientation of the rigid structure.

To date, there have been no prior art devices, systems and methods that have a flexible sheet array of electrodes that is adaptable to varying surfaces of organs within a patient's body, particularly useful for diagnosing and treating electrical abnormalities of the heart and/or vessels of the patient's body in just one particular medical application by way of example. It is important to note that the present invention is directed to a medical device that is particularly useful for any type of medical application requiring diagnosis and/or treatment of tissue or biological function requiring electrical signal processing using a flexible sheet array of electrodes that is adaptable to varying surfaces of organs within a patient's body which is not found anywhere in prior art devices.

SUMMARY OF THE INVENTION

The present invention is directed to a medical device comprising a flexible elongated body, a handle connected to the elongated body, at least one spine connected to the elongated body, and a flexible sheet attached to the at least one spine. The flexible sheet has a plurality of electrodes thereon, wherein the flexible sheet and the plurality of electrodes define a mapping assembly for mapping electrical information in tissue, and wherein the at least one spine and the flexible sheet is movable from a collapsed configuration to a deployed configuration.

The present invention is also directed to a method for mapping tissue comprising the steps of providing a device comprising a flexible elongated body; a handle connected to the elongated body; at least one spine connected to the elongated body; and a flexible sheet attached to the at least one spine. The flexible sheet has a plurality of electrodes thereon, wherein the flexible sheet and the plurality of electrodes define a mapping assembly for mapping electrical information in tissue, and wherein the at least one spine and the flexible sheet are movable from a collapsed configuration to a deployed configuration. The mapping assembly is conformed to the tissue when the device is in the deployed configuration; and electrical information from the tissue is provided using the plurality of electrodes; and a map with the electrical information is formed.

The present invention will be more fully understood from the following detailed description of the embodiments thereof, taken together with the drawings in which:

DETAILED DESCRIPTION OF THE INVENTION

Figure 1A:
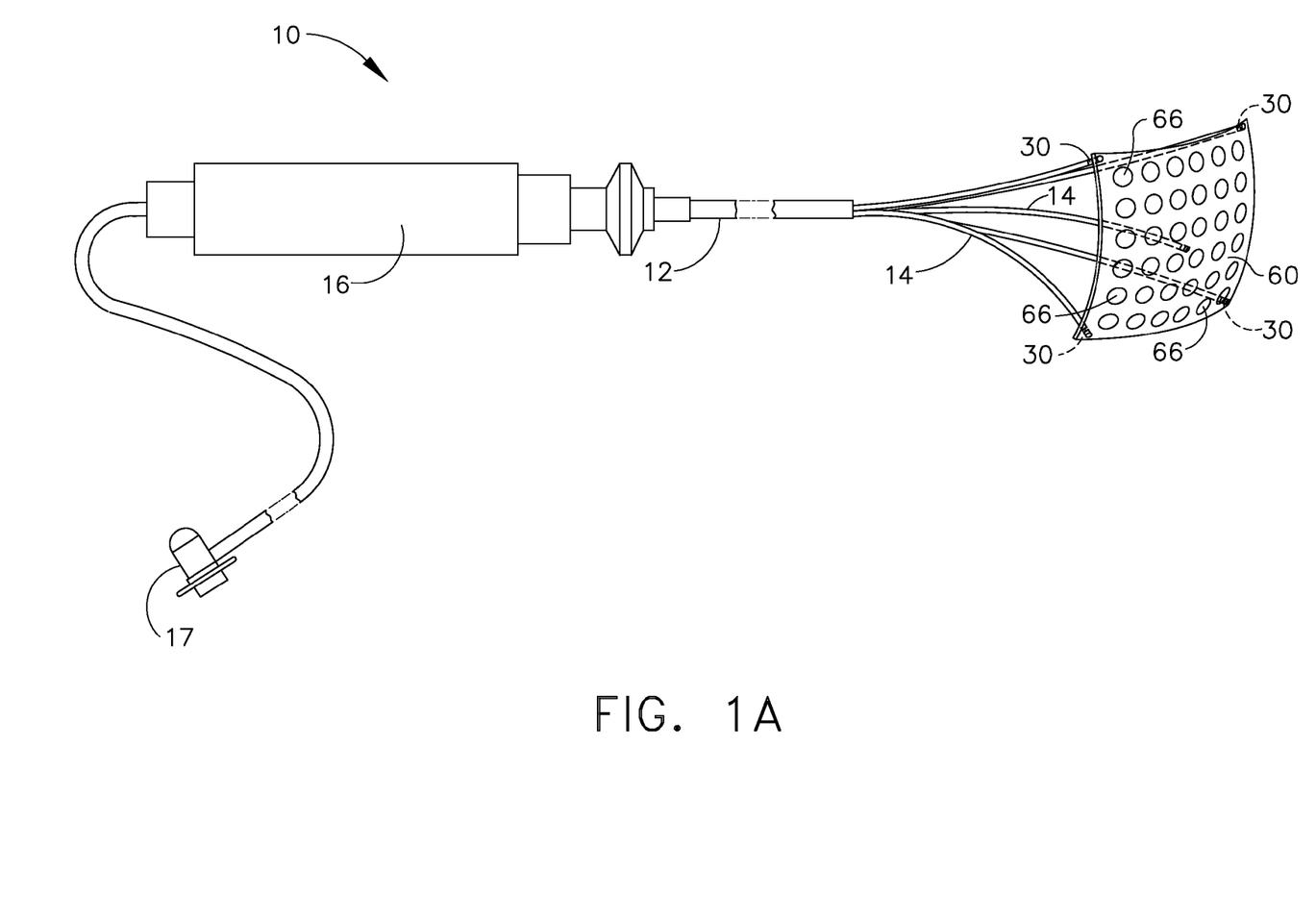
FIG. 1A is a schematic, pictorial illustration of a catheter with a flexible sheet array of electrodes, in accordance with an embodiment of the present invention.

The invention is directed to a catheter having a mapping assembly comprising a plurality of spines, for example, as disclosed in U.S. Pat. No. 6,961,602, the disclosure of which is incorporated herein by reference, which has a number of like features and function used in the present invention. The same reference numerals are used to designate the same or similar features or parts. As shown in FIG. 1, the catheter 10 comprises a flexible, elongated catheter body 12 having proximal and distal ends, a control handle 16 at the proximal end of the catheter body 12, and a mapping assembly 18 comprising at least one spine 14 or a plurality of spines 14 mounted at the distal end of the catheter body 12.

Figure 1B:
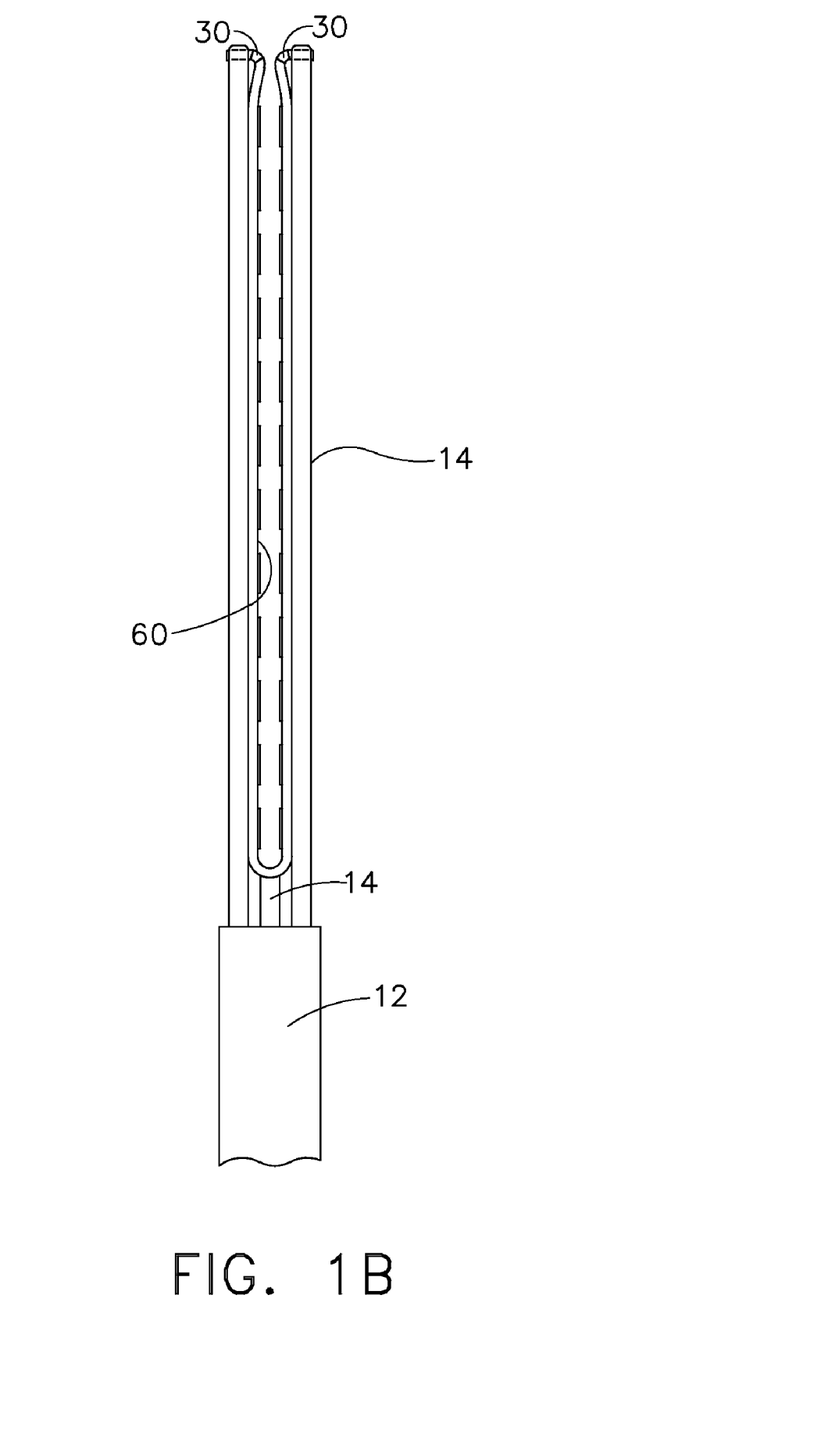
FIG. 1B is a view of the catheter of FIG. 1A in its pre-deployed, collapsed configuration, in accordance with the present invention.
Figure 2:
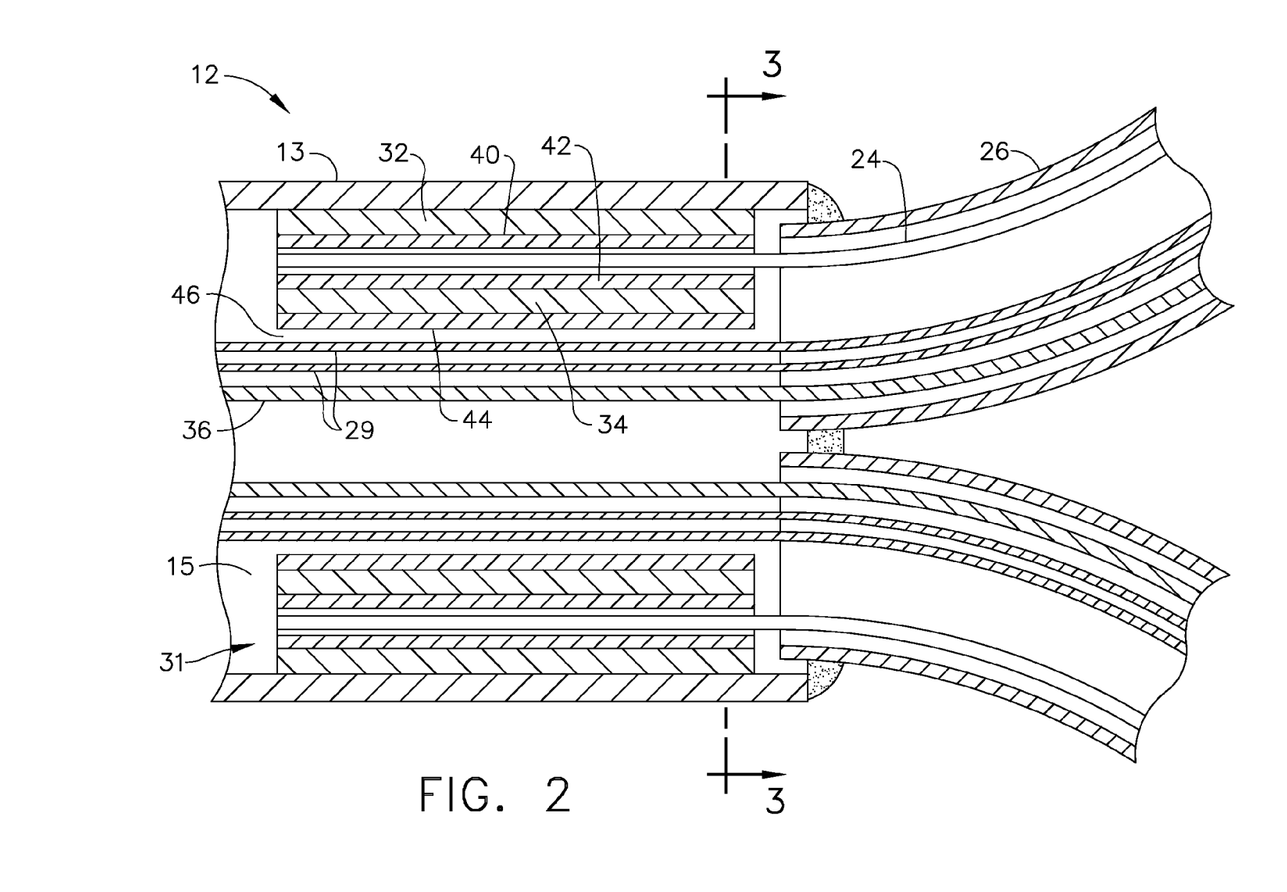
FIG. 2 is a schematic, sectional view showing details of the catheters of FIG. 1A and FIG. 1B, in accordance with an embodiment of the present invention.

As shown in FIGS. 1A, 1B and 2, the catheter body 12 comprises an elongated tubular construction having a single, axial or central lumen 15, but can optionally have multiple lumens along all or part of its length if desired. The catheter body 12 is flexible, i.e., bendable, but substantially non-compressible along its length. The catheter body 12 can be of any suitable construction and made of any suitable material. A presently preferred construction of the catheter body 12 comprises an outer wall 13 made of polyurethane or PEBAX™. (polyether block amide). The outer wall 13 comprises an imbedded braided mesh of stainless steel or the like, as is generally known in the art, to increase torsional stiffness of the catheter body 12 so that, when the control handle 16 is rotated, the distal end of the catheter body 12 will rotate in a corresponding manner.

The length of the catheter body 12 is not critical, but preferably ranges from about 90 cm to about 120 cm, and more preferably is about 110 cm. The outer diameter of the catheter body 12 is also not critical, but is preferably no more than about 8 french, more preferably about 7 french. Likewise, the thickness of the outer wall 13 is not critical, but is preferably thin enough so that the central lumen 15 can accommodate puller wires, lead wires, sensor cables and any other wires, cables or tubes. If desired, the inner surface of the outer wall 13 is lined with a stiffening tube (not shown) to provide improved torsional stability. An example of a catheter body construction suitable for use in connection with the present invention is described and depicted in U.S. Pat. No. 6,064,905, the entire disclosure of which is incorporated herein by reference.

Figure 4:
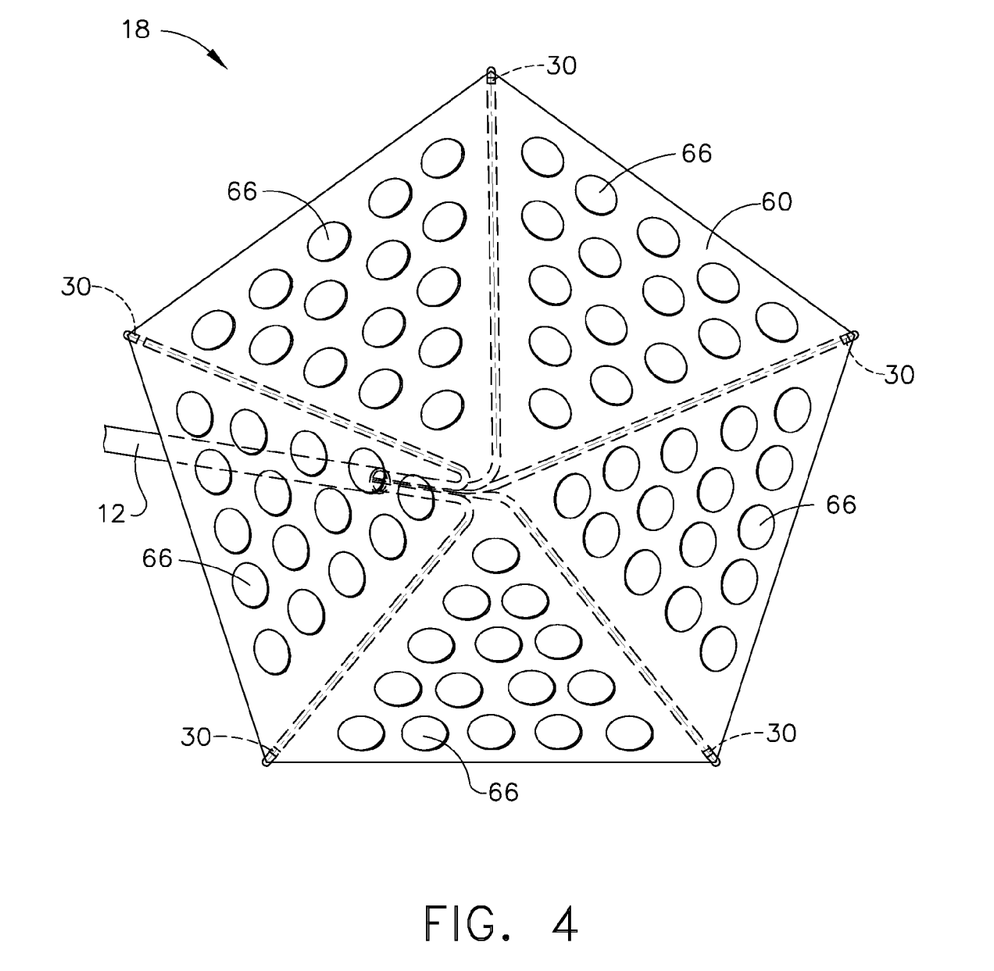
FIG. 4 is a schematic, pictorial illustration of the distal end of a catheter with a flexible sheet array of electrodes, in accordance with an alternative embodiment of the present invention.

In the depicted embodiment, the mapping assembly 18 comprises at least one spine 14 or a plurality of spines 14, for example four spines in some embodiments or five spines in other embodiments. For example, as shown in FIGS. 1A and 1B, catheter 10 comprises five spines including a central spine 14 that is used for collapsing mapping assembly 18 as best shown in FIG. 1B. In these embodiments, central spine 14 is either shorter in length than the other spines 14, for example the spines 14 connected at each corner of the mapping assembly 18 or is configured to be withdrawn prior to the other spines 14 for efficient collapsing of the mapping assembly 18. Catheter 10 is not limited to any particular number of spines and comprises at least one spine, two or more spines, three or more spines, four or more spines, or five or more spines, etc. The exact number of spines is not important so long that the one or more spines 14 is/are capable of supporting the sheet array 60. It is also important to note that the sheet array 60 can be divided into a plurality of distinct separate sections that are deployed into a final configuration in the form a unitary-like final form or shape, i.e. final configuration appears as a single sheet design even though the sheet array 60 is made up of a plurality of distinct, separate sections as best illustrated in FIG. 4.

Each spine 14 optionally carries at least one location sensor 30 and, is connected at its distal end to the sheet array 60 comprising a matrix of electrodes 66. And, when the sheet matrix is deployed (FIG. 1A and FIG. 5) the spines 14 position the sheet array 60 and its matrix of electrodes 66 in contact with heart tissue, wherein the electrodes 66 of the matrix are capable of obtaining electrical, mechanical and location/position data which is used for forming a map of the tissue which displays one or more of the electrical, mechanical and location/position data.

Each spine 14 has a proximal end attached at the distal end of the catheter body 12 and a distal end attached to the sheet array 60 thereby defining the mapping assembly 18. Each spine 14 contains a support arm (FIG. 2) comprising a metal or plastic material that has shape memory, such that the support arm 24 forms an initial shape when no external forces are applied, forms a deflected shape when an external force is applied, and returns to its initial shape when the external force is released. In a preferred embodiment, the support arm 24 comprises a superelastic material, for example a nickel-titanium alloy, such as Nitinol. Each spine 14 also comprises a non-conductive covering 26 in surrounding relation to the support arm 24. In a preferred embodiment, the non-conductive covering 26 comprises a biocompatible plastic tubing, such as a polyurethane or polyimide tubing.

As will be recognized by one skilled in the art, the number of spines 14 can vary as desired depending on the particular application, so that the catheter 10 preferably has at least one spine or a plurality of spines, preferably at least two, three, four or five spines, and in some instances, preferably at least five or more spines or as many as eight or more spines in some instances.

As described in more detail below, the spines 14 are moveable between an expanded or deployed arrangement, wherein, for example, each spine extends radially outwardly from the catheter body 12 when moved or deployed to its final configuration (FIG. 1A and FIG. 4), or the spines 14 may be arranged in a collapsed arrangement (pre-deployment configuration), as best shown in FIG. 1B, wherein, for example, each spine 14 is disposed generally along a longitudinal axis of the catheter body 12 so that the spines 14 are capable of fitting within a lumen of a guiding sheath, as discussed further below.

The mapping assembly 18 comprises the sheet array 60 and its matrix array of electrodes 66 at the distal end of a catheter 10. As shown, the electrodes 66 are printed or otherwise fixed to the flexible sheet 60, with respective conductors 29 (FIG. 2 and FIG. 3) electrically connected or operatively connected to the electrodes 66 at their distal end and connector 17 at their proximal end (FIG. 1A). The connector 17 is connected to a controller (not shown) such as the CARTO® mapping and navigation system (manufactured and sold by Biosense Webster, Inc., Diamond Bar, Calif.). In certain embodiments according to the present invention, the corners of the sheet 60 are held by the distal ends of spines or arms 14 which extend from the distal end of the insertion tube 12. In other embodiments, the distal ends of spines or arms 14 are connected at other areas of the sheet 60 instead of the corners, for example, along an edge of sheet 60 or in central portion of sheet 60 (such as a midpoint) or another location on sheet 60 off centered from the midpoint.

While the catheter 10 is being inserted into the patient's body and navigated to the desired location in the heart using the position sensors 30, the spines 14 are held close together in its collapsed or pre-deployment configuration (FIG. 1B), and the sheet 60 of electrodes 66 is therefore collapsed between the spines 14, as shown.

When the catheter reaches the desired location, the arms 14 are deployed to spread apart to its deployed or final configuration (FIG. 1A and FIG. 4), thereby stretching open the sheet 60 of electrodes 66, as shown in these FIGS. In the deployed configuration, the catheter 10 is advanced toward the heart wall, so that all (or at least most) of the electrodes 66 of the sheet array 60 contact the wall simultaneously. Each electrode can then sense the local electrical signals of the heart tissue, and the system console can process the entire array of signals to give an extended, real-time picture of electrical activity.

The sheet array 60 supporting the electrodes 66 is elastic in form (which is described in greater detail below) to enable it to conform to the heart wall. The sheet array 60 is either a single sheet (unitary design) such as depicted in FIG. 1A or is made of separate, distinct sheet sections that are deployed as a unitary-like design in its final form (FIG. 4). Additionally, the sheet array 60 is customizable to any desired final shape or configuration in order to conform to particular anatomy within the heart chamber or other organ or vessel of the body including the ostium of the pulmonary vein in order to conduct mapping and ablation procedures of the pulmonary vein. For example, the final configuration of the sheet array 60 is circular, spherical, oblong, square, rectangular, trapezoidal, triangular or other desired shape or form including asymmetrical shapes as well as a final configuration in three-dimensional configuration such as substantially concave or convex forms. The sheet array 60 can bow slightly outward (convex shape) to improve contact with and conform to concave regions of the heart wall.

Sheet array 60 is preferably made of SU-8 which is a high contrast, epoxy based photoresist designed for micromachining and other microelectronic applications, where a thick, chemically and thermally stable image is desired. SU-8 is a negative, epoxy-type, near-UV photoresist based on EPON SU-8 epoxy resin (from Shell Chemical) that has been originally developed, and patented by IBM Corporation in U.S. Pat. No. 4,882,245, the disclosure of which is incorporated by reference herein.

This photoresist 60 can be as thick as 2 mm and aspect ratio >20 and higher have been demonstrated with a standard contact lithography equipment. These astounding results are due to the low optical absorption in the UV range which only limits the thickness to 2 mm for the 365 nm-wavelength where the photo-resist is the most sensitive (i.e., for this thickness very little UV light reach the bottom of the structure). The sheet array 60 will undoubtedly benefit from this resist that is well suited for acting as a mold for electroplating because of its relatively high thermal stability (Tg>200° C. for the cross-linked (i.e., exposed) resist). SU-8 is commercially available from companies such as MicroChem Inc. (previously Microlithography Chemical Corp., Newton, Mass.) under the name "SU-8 . . . " with each SU-8 variant/product having different viscosities ("SU-8 5"; "SU-8 10"; "SU-8 25"; "SU-8 50"; "SU-8 100") and also the "SU-8 2000", "SU-8 3000", etc. where the standard GBL solvent is replaced by cyclopentanone and has improved properties, Gersteltec SARL (Pully, Switzerland).

SU-8 2000 is one particular variant that is particularly useful for the sheet array 60 because it is an improved formulation of SU-8, which has been widely used by MEMS (microelectronic materials) producers for many years. The use of a faster drying, more polar solvent system results in improved coating quality and increases process throughput. SU-8 2000 is available in twelve standard viscosities. Film thicknesses of 0.5 to >200 microns can be achieved with a single coat process. The exposed and subsequently thermally cross-linked portions of the film are rendered insoluble to liquid developers. SU-8 2000 has excellent imaging characteristics and is capable of producing very high aspect ratio structures. SU-8 2000 has very high optical transmission above 360 nm, which makes it ideally suited for imaging near vertical sidewalls in very thick films. SU-8 2000 is best suited for permanent applications where it is imaged, cured and left on the device, i.e. array 60 of the mapping device 18.

SU-8 2000 photoresist is most commonly exposed with conventional UV (350-400 nm) radiation, although i-line (365 nm) is the recommended wavelength. SU-8 2000 may also be exposed with e-beam or x-ray radiation. Upon exposure, cross-linking proceeds in two steps (1) formation of a strong acid during the exposure step, followed by (2) acid-catalyzed, thermally driven epoxy cross-linking during the post exposure bake (PEB) step. A normal process is: spin coat, soft bake, expose, PEB, followed by develop. A controlled hard bake is recommended to further cross-link the imaged SU-8 2000 structures when they will remain as part of the device. The entire process should be optimized for the specific application.

As substrate preparation, in order to obtain maximum process reliability, substrates of matrix array 60 should be clean and dry prior to applying SU-8 2000 resist. For best results, substrates should be cleaned with a piranha wet etch (using $H_2SO_4$ & $H_2O_2$) followed by a de-ionized water rinse. Substrates may also be cleaned using reactive ion etching (RIE) or any barrel asher supplied with oxygen. Adhesion promoters are typically not required. For applications that include electroplating, a pre-treatment of the substrate with MCC Primer 80/20 (HMDS) is recommended.

Coat. SU-8 2000 resists are available in many standard viscosities such as those mentioned above. The recommended program for the fabrication/coating method comprises: Dispense 1 ml of resist for each inch (25 mm) of substrate diameter; Spin at 500 rpm for 5-10 seconds with acceleration of 100 rpm/second; Spin at 2000 rpm for 30 seconds with acceleration of 300 rpm/second.

Edge Bead Removal (EBR). During the spin coat process step, a build-up of photoresist may occur on the edge of the substrate. In order to minimize contamination of the hotplate, this thick bead should be removed. This can be accomplished by using a small stream of solvent (MicroChem's EBR PG) at the edge of the wafer either at the top or from the bottom. Most automated spin coaters now have this feature and can be programmed to do this automatically. By removing any edge bead, the photo mask can be placed into close contact with the wafer, resulting in improved resolution and aspect ratio.

Soft Bake. A level hotplate with good thermal control and uniformity is recommended for use during the Soft Bake step of the process. Convection ovens are not recommended. During convection oven baking, a skin may form on the resist. This skin can inhibit the evolution of solvent, resulting in incomplete drying of the film and/or extended bake times. Note: To optimize the baking times/conditions, remove the wafer from the hotplate after the prescribed time and allow it to cool to room temperature. Then, return the wafer to the hotplate. If the film 'wrinkles', leave the wafer on the hotplate for a few more minutes. Repeat the cool-down and heat-up cycle until 'wrinkles' are no longer seen in the film.

Exposure. To obtain vertical sidewalls in the SU-8 2000 resist, it is recommended to use a long pass filter to eliminate UV radiation below 350 nm. With the recommended filter (PL-360-LP) from Omega Optical (www.omegafilters.com) or Asahi Technoglass filters V-42 plus UV-D35 (www.atgc.co.jp), an increase in exposure time of approximately 40% is required to reach the optimum exposure dose. Note: With optimal exposure, a visible latent image will be seen in the film within 5-15 seconds after being placed on the PEB hotplate and not before. An exposure matrix experiment should be performed to determine the optimum dosage.

Development. PEB should take place directly after exposure. After 1 minute of PEB at 95° C., an image of the mask should be visible in the SU-8 2000 photoresist coating. If no visible latent image is seen during or after PEB this means that there was insufficient exposure, heating or both. SU-8 2000 photoresist has been designed for use in immersion, spray or spray-puddle processes with MicroChem's SU-8 developer. Other solvent based developers such as ethyl lactate and diacetonealcohol may also be used. Strong agitation is recommended when developing high aspect ratio and/or thick film structures. Note: The use of an ultrasonic or megasonic bath may be helpful when developing out via or hole patterns or structures with tight pitch.

Rinse and Dry. When using SU-8 developer, spray and wash the developed image with fresh solution for approximately 10 seconds, followed by a second spray/wash with Isopropyl Alcohol (IPA) for another 10 seconds. Air dry with filtered, pressurized air or nitrogen. Note: A white film produced during IPA rinse is an indication of underdevelopment of the unexposed photoresist. Simply immerse or spray the substrate with additional SU-8 developer to remove the white film and complete the development process. Repeat the rinse step. The use of an ultrasonic or megasonic bath will energize the solvent and allow for more effective development of the unexposed resist.

Properties/Hard Bake (cure). SU-8 2000 has good mechanical properties. However, for applications where the imaged resist is to be left as part of the final device, a hard bake can be incorporated into the process. This is generally only required if the final device or part is to be subject to thermal processing during regular operation such as is the case as a mapping and treatment device 18 wherein the sheet array 60 has a matrix of microelectrodes 66. A hard bake or final cure step is added to ensure that SU-8 2000 properties do not change in actual use. SU-8 2000 is a thermal resin and as such its properties can continue to change when exposed to a higher temperature than previously encountered. It is recommend to use a final bake temperature 10° C. higher than the maximum expected device operating temperature. Depending on the degree of cure required, a bake temperature in the range of 150° C. to 250° C. and for a time between 5 and 30 minutes is typically used. Note: The hard bake step is also useful for annealing any surface cracks that may be evident after development. The recommended step is to bake at 150° C. for a couple of minutes. This applies to all film thicknesses.

In general, the SU-8 material of the sheet array 60 consists of chemically amplified; epoxy based negative resists with high functionality, high optical transparency and are sensitive to near UV radiation. Cured films or topography are highly resistant to solvents, acids and bases and have excellent thermal stability, making it well suited for permanent use applications especially as a matrix of microelectrodes 66 for mapping and treatment of tissue in patient's body.

For example, attributes of SU-8 2000 are as follows:
>10:1 aspect ratio imaging with vertical sidewalls;
<1 um to >200 um in a single spin coat;
High chemical and plasma resistance; and
Faster Drying Films.

Attributes of SU-8 3000 are as follows:
5:1 aspect ratio imaging with vertical sidewalls;
Up to 100 um in a single spin coat;
High chemical and plasma resistance; and
Enhanced adhesion.

Each electrode 66 of the matrix 60 has an exposed length preferably ranging from about 0.5 mm to about 4 mm, more preferably from about 0.5 mm to about 2 mm, still more preferably about 1 mm.

The electrodes 66 are printed or otherwise fixed to the flexible sheet 60, with respective lead wire/conductor 29 connected to each electrode 66. Portions of the sheet 60, such as the corners of the sheet 60, are held by the distal ends of multiple spines 14, such as the arms of the PENTARAY™ catheter (FIG. 4), which extend from the distal end of the insertion tube 12.

While the catheter 10 is being inserted into the patient's body and navigated to the desired location in the heart, the spines 14 are held close together in a pre-deployed configuration (FIG. 1B), and the sheet of electrodes 60 is therefore collapsed between them, as shown. When the catheter reaches the desired location, the spines 14 are deployed to spread apart, thereby stretching open the sheet of electrodes, as shown in FIG. 1A or opening the multiple, distinct/separate sections of the sheet array 60 (FIG. 4).

In these deployed configurations, the catheter 10 is advanced toward the heart wall, so that all (or at least most) of the electrodes 66 contact the heart wall simultaneously. Each electrode 66 can then sense the local electrical signal, and the system console can process the entire array of signals to give an extended, real-time picture of electrical activity. This electrical information is provided along with location and mechanical information as described below in order to provide accurate maps of the properties of the heart tissue at these locations.

Since the sheet array 60 is made of SU-8 material, the electrodes 66 are properly supported within the photoresist and is sufficiently elastic to enable it to conform to the heart wall or other features of the heart, vessels or anatomy, in any desired final/deployed configuration. In certain instances, sheet array 60 may bow slightly outward (convex configuration) to improve contact with concave regions of the heart wall as just one example of the customizability of the sheet array 60.

A preferred method for attaching a lead wire 29 to the photoresist material of the sheet array 60 involves first making a small hole through an outer wall of the non-conductive covering 26. Such a hole can be created, for example, by inserting a needle through the non-conductive covering 26 and heating the needle sufficiently to form a permanent hole. The lead wire 29 is then drawn through the hole by using a microhook or the like. The end of the lead wire 29 is then stripped of any coating and welded to the underside of the photoresist material of sheet array 60, which is then slid into position over the hole and fixed in place with polyurethane glue or the like.

Each spine 14 also optionally includes at least one location sensor 30 (FIG. 1A and FIG. 1B). The location sensor 30 is mounted near the distal end of each spine 14. In the depicted embodiment, a location sensor 30 is mounted such that the distal end of the location sensor 30 is secured within its corresponding spine 14, while the proximate end of the location sensor 30 extends into the distal end of the non-conductive covering 26. Each location sensor 30 is used to determine the six-dimensional coordinates (X,Y,Z axis directions and yaw, pitch and roll orientations) of its corresponding spine 14 and attached portion of the sheet array 60 as the electrodes 66 are being used to collect electrical mapping data at the measured six-dimensional location coordinates (position and orientation coordinates). As a result, both electrical and location data are obtained for each data point that is mapped by the sheet array 60.

Each location sensor 30 is connected to a corresponding sensor cable 36. Each sensor cable 36 extends through the non-conductive covering 26, catheter body 12 and control handle 16 and out the proximal end of the control handle 16 within an umbilical cord (not shown) to a sensor control module (not shown) that houses a circuit board (not shown). Alternatively, the circuit board can be housed within the control handle 16, for example, as described in U.S. Pat. No. 6,024,739, the disclosure of which is incorporated herein by reference.

Each sensor cable 36 comprises multiple wires encased within a plastic covered sheath. In the sensor control module, the wires of the sensor cable 36 are connected to the circuit board. The circuit board amplifies the signal received from the corresponding location sensor 30 and transmits it to a computer in a form understandable by the computer by means of a sensor connector at the proximal end of the sensor control module.

Preferably each location sensor 30 is an electromagnetic location sensor. For example, each location sensor 30 comprises one or more magnetic-field-responsive coils, as described in U.S. Pat. No. 5,391,199, or a plurality of such coils, as described in International Publication WO 96/05758. The plurality of coils enables the six-dimensional coordinates (i.e. the three positional, X, Y, and Z axis directions and the three orientation coordinates, yaw, pitch and roll orientations) of the location sensor 30 to be determined. Alternatively, any suitable location sensor known in the art maybe used, such as electrical, magnetic or acoustic sensors. Suitable location sensors for use with the present invention are also described, for example, in U.S. Pat. Nos. 5,558,091, 5,443,489, 5,480, 422, 5,546,951, and 5,568,809, and International Publication Nos. WO 95/02995, WO 97/24983, and WO 98/29033, the disclosures of which are incorporated herein by reference. A particularly preferred location sensor 30 is a single axis sensor having a length ranging from about 3 mm to about 7 mm, preferably about 4 mm, such as that described in the U.S. patent application Ser. No. 09/882,125 filed Jun. 15, 2001, entitled "Position Sensor Having Core with High Permeability Material," the disclosure of which is incorporated herein by reference. Smaller sensors are particularly desirable for use in the present invention because of the need to keep the diameters of the spines 14 small enough so that they all fit within the lumen of a guiding sheath.

Figure 3:
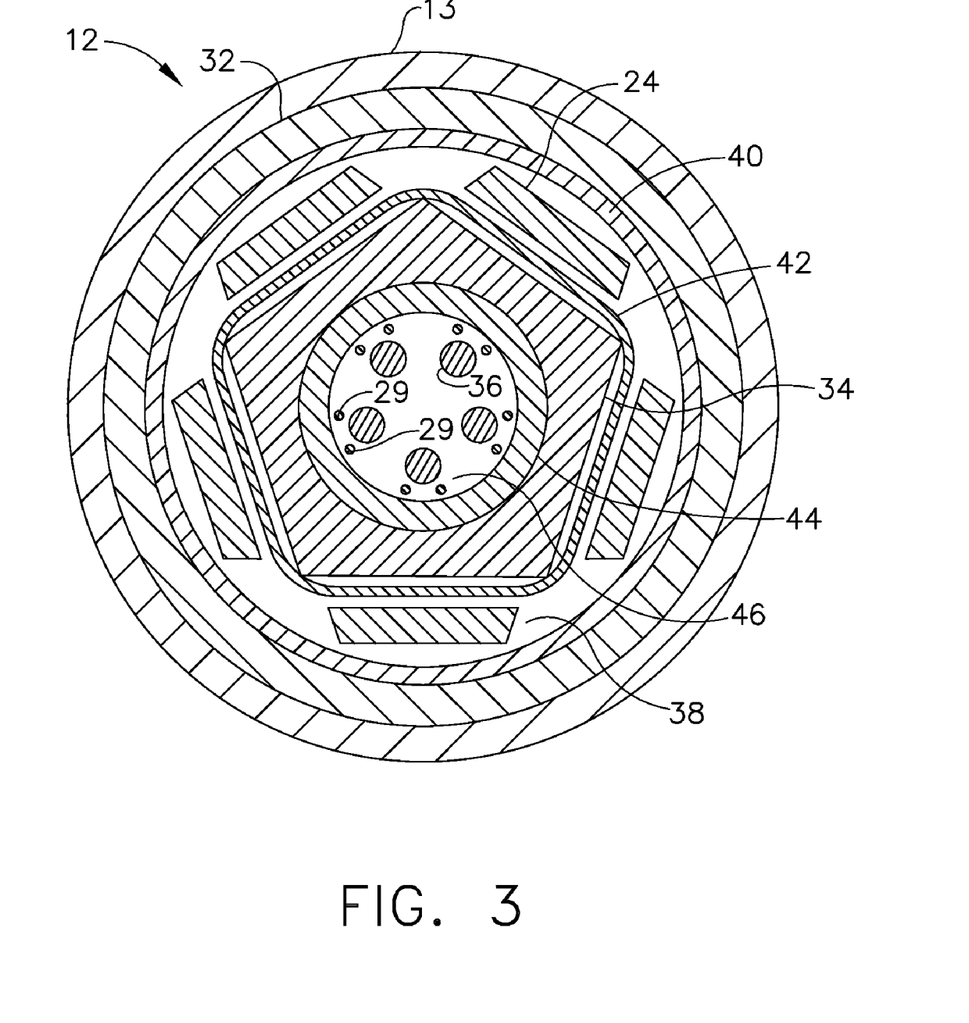
FIG. 3 is a cross-sectional view of an alternative embodiment of the catheter of FIG. 1A and FIG. 1B taken along line 3-3 of FIG. 2 in accordance with the present invention.

A suitable construction of the distal end of the catheter body 12, having spines 14 mounted thereto, is depicted in FIGS. 2 and 3. For clarity, only two spines 14 are shown in FIG. 2. Mounted in the distal end of the lumen 15 of the catheter body 12 is a spine mounting assembly 31. The spine mounting assembly 31 comprises an outer mounting ring 32 disposed within the outer wall 13 of the catheter body 12. The outer mounting ring 32 preferably comprises a metal material, such as stainless steel, more particularly stainless steel 303, and may be attached at the distal end of the catheter body 12 by a variety of methods, such as by welding or by use of an adhesive, such as a polyurethane glue. Alternatively, the outer mounting ring 32 may comprise a plastic material. A mounting structure 34 is provided coaxially within the outer mounting ring 32. In the depicted embodiment, the mounting structure 34 is multi-sided and comprises a metal material, such as stainless steel, more particularly stainless steel 303. The mounting structure 34 may also alternatively comprise a plastic material. The outer mounting ring 32 and the mounting structure 34 provide a channel 38 in which the proximal end of each support arm 24 is mounted. Specifically, each spine 14 is mounted in the catheter body 12 by removing a portion of the non-conductive covering 26 at the proximal end of each spine 14, inserting the distal end of each support arm 24 into the channel 38 between the outer mounting ring 32 and the multi-sided mounting structure 34 and affixing each support arm 24 within the channel 38 by any suitable means, such as with a polyurethane glue or the like.

In a one embodiment, the support arm 24 has a generally trapezoidally-shaped end cross section with curved sides. In such an arrangement, when each support arm 24 is inserted into the channel 38, a substantially flat surface of each support arm 24, preferably the base of the trapezoidally-shaped end cross section, is mounted against a substantially flat surface on the multi-sided mounting structure 34. Preferably the number of substantially flat outer surfaces on the multi-sided mounting structure 34 corresponds to the number of spines 14. In such an instance, the support arm 24 of each spine 14 maybe mounted within the channel 38 and adjacent to its corresponding side on the multi-sided mounting structure 34 to enable the support arms 24, and thus the spines 14, to be equally spaced around the multi-sided mounting structure 34. The multi-sided mounting structure 34 may be approximately co-axial with the longitudinal axis of the catheter body 12 such that the spines 14 are equally spaced about the catheter body 12 as well. Once each support arm 24 is properly positioned within the channel 38, each support arm 24 may be affixed within the channel 38 by any suitable means, such as by use of an adhesive, such as a polyurethane glue. Alternatively, the mounting structure 34 can have a round outer surface, although with such an embodiment more care needs to be taken if the support arms 24 are to be evenly spaced about the mounting structure.

In the depicted embodiment, a first non-conducting tube 40 is disposed between the outer mounting ring 32 and the support arms 24, and a second non-conducting tube 42 is disposed between the support arms 24 and the mounting structure 34. The non-conducting tubes 40 and 42, which may be polyimide tubes, ensure that each support arm 24 remains electrically isolated. In addition, a mounting ring inner tube 44 is secured within the mounting structure 34. The mounting ring inner tube 44 preferably comprises a non-conducting material such as polyimide. The mounting ring inner tube 44 defines a mounting ring lumen 46 through which each of the electrode lead wires 29 and sensor cables 36 extend.

As previously discussed, when mounting the support arms 24 to the spine mounting assembly 31, a portion of the non-conductive covering 26 at the proximal end of each spine 14 is removed to expose the support arm 24. Removing a portion of the non-conductive covering 26 at the proximal end of each spine 14 enables the electrode lead wires 29 and sensor cables 36, corresponding to the sheet array 60, the electrodes 66 and location sensor 30, to extend from the lumen 15 of the catheter 12, through the mounting ring lumen 46, and into each non-conductive covering 26.

Once inserted into the non-conductive coverings 26, the electrode lead wires 29 and sensor cables 36 extend within the non-conductive covering 26 and are electrically connected at their distal ends to their corresponding portions on the sheet array 60, electrodes 66 and location sensor 30 respectively.

To use the catheter 10 of the invention, a cardiologist or electrophysiologist introduces a guiding sheath and a dilator into the patient, as is generally known in the art, so that the distal ends of the sheath and dilator are in the region of the heart to be mapped. In some instances, such as when it is desired to insert the catheter 10 into the left ventricle through the aortic valve in a direction opposite the blood flow, it is preferable to use a pigtail-shaped dilator (not shown). Specifically, the side of the loop of the dilator is pushed against the flaps of the valve and serves essentially as a blunt instrument to push the flaps inward so that they are temporarily inverted while the dilator and guiding sheath are advanced through the valve. By using the surface of the loop to push the flaps of the valve, potential puncturing of the flaps of the valve can be avoided. In contrast, pushing the flaps with a dilator having a straight distal end can potentially puncture or otherwise damage the flaps. After the dilator and guiding sheath having been advanced through the valve with the loop inside the left ventricle, the flaps of the aortic valve return to their original, natural position.

Thereafter, the dilator is removed from the guiding sheath, and the catheter 10 is introduced into the patient through the guiding sheath. To insert the catheter 10 into the guiding sheath, the mapping assembly must be in its collapsed arrangement (FIG. 1B), wherein each spine 14 is disposed generally along the longitudinal axis of the catheter body 12. A suitable guiding sheath for use in connection with the catheter 10 is the PREFACE™ Braided Guiding Sheath (commercially available from Biosense Webster, Inc., Diamond Bar, Calif.). Such a guiding sheath has sufficient strength to hold each support arm 24 in the collapsed arrangement, such that the spines 14 and also the entire remainder of the catheter 10 can travel within the guiding sheath, from an insertion point in the patient, through a vein or artery and to a desired location in the heart. Once the distal end of the catheter has reached the desired location, such as a position within the left ventricle of the heart, relative longitudinal movement between the catheter 10 and the guiding sheath is provided to allow at least a portion of each spine 14 to protrude from the guiding sheath. Preferably the guiding sheath is moved proximally relative to the distal end of the catheter to expose the spines 14. When a portion of each spine 14 protrudes from the guiding sheath and a compression force is no longer applied by the guiding sheath on the spines, the shape memory of the support arms 24 allows the support arms to revert to a first expanded arrangement as best shown in FIG. 1A and FIG. 4 (alternative embodiment wherein the sheet array matrix is in separate, distinct sections).

In the first expanded arrangement, at least a number of electrodes from sheet array 60 are placed into contact with the heart tissue such that electrical, location and mechanical information are obtained from the contacted heart tissue. The spines 14 can then be manipulated by the using control handle 16 to reposition the sheet array 60 to additional expanded arrangements to contact other portions of the heart tissue such that electrical, location and mechanical information can be obtained from these sections of the tissue as well. This repositioning is preferably achieved by further moving the guiding sheath proximally relative to the catheter to thereby expose a greater portion of each spine. In the depicted embodiment, the more of each spine that is exposed, the further each spine can bend or expand away from the catheter thereby allowing the sheet array 60 to form to its final, deployed configuration or shape to thereby contact heart tissue. This process can be repeated until the heart has been satisfactorily mapped.

The expanded arrangement of spines 14 and sheet array 60 can take on various shapes. For instance, in the above-described embodiment, each spine 14 extends radially outwardly from the catheter body 12 and forms an outwardly curved shape as shown in FIG. 1A. In other embodiments, each spine 14 extends radially outwardly from the catheter body 12 and results in the sheet array 60 being substantially concave or substantially convex in final form.

Using the inventive catheter 10 having multiple spines 14 connected to sheet array 60 for electrical and mechanical mapping and location sensing (position determination) capabilities, the physician, such as a cardiologist or electrophysiologist, can map local activation time and obtain voltage maps. The cardiologist can also determine those locations (with six-dimensional degrees of accuracy) in the heart having no mechanical activity by monitoring whether the position of the location sensor 30 changes over a complete cardiac cycle, i.e. determining mechanical information. This information can guide the physician in providing therapy to the patient. For example, where the physician finds regions of the heart that do not have mechanical activity, he or she can revascularize those regions using known techniques, such as gene, cell, protein or drug therapy for example using the MYOSTAR™ injection catheter (manufactured and sold by Biosense Webster, Inc., Diamond Bar, Calif.). The inventive catheter 10 allows the physician to map the heart more quickly with the sheet array 60 and its matrix of electrodes 66 than traditional catheters by measuring multiple points of data at a time.

If desired, the catheter may include a steering mechanism for deflection of the distal end of the catheter body 12. With such a design, the distal end of the catheter body 12 preferably comprises a short length of tubing, e.g., 2 to 4 inches in length, that is more flexible than the remainder of the catheter body 12. A suitable steering mechanism comprises a puller wire (not shown) that extends from a proximal end in the control handle 16, through the central lumen 15 in the catheter body 12 and into an off axis lumen in the short length of tubing. Within the catheter body 12, the puller wire extends through a closely wound coil that is bendable but substantially non-compressible. The coil is fixed near the proximal and distal ends of the catheter body 12 and prevents deflection of the catheter body 12. The distal end of the puller wire is anchored at the distal end of the short length of tubing in the off axis lumen. The proximal end of the puller wire is anchored to a movable member in the handle 16 that can be moved relative to the catheter body 12. Proximal movement of the movable member relative to the catheter body 12 results in deflection of the short length of tubing. An example of such a steering mechanism and construction is described in more detail in U.S. Pat. No. 6,064,905, the disclosure of which is incorporated herein by reference. When incorporating a steering mechanism into the inventive catheter 10, it may be desirable to include a location sensor 30 at the distal end of the catheter body 12. As would be recognized by one skilled in the art, of a slurring mechanism is not including, the handle 16 can be eliminated, although it is described to maintain the handle for ease of use by the physician.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A medical device comprising:
   a flexible elongated body;
   a handle connected to the elongated body;
   a plurality of spines connected to the elongated body;
   a flexible sheet having a plurality of electrodes thereon, the flexible sheet and the plurality of electrodes defining a mapping assembly for mapping electrical information in tissue, wherein each of the plurality of spines is attached near a respective corner of the flexible sheet with the spines and the flexible sheet being movable from a collapsed configuration to a deployed configuration; and
   a central spine shorter in length than the plurality of spines which is connected to the flexible sheet at a location near the center of the sheet.

2. The medical device according to claim 1, further comprising a location sensor on the at least one of the plurality of spines.

3. The medical device according to claim 2, wherein the location sensor provides six-dimensional location information.

4. The medical device according to claim 3, wherein the mapping assembly provides mechanical information.

5. The medical device according to claim 1, wherein the plurality of electrodes are an array of electrodes on the flexible sheet.

6. The medical device according to claim 5, wherein the mapping assembly comprises a photoresist.

7. The medical device according to claim 6, wherein the photoresist comprises SU-8 material.

8. The medical device according to claim 1, wherein the plurality of spines comprises two or more spines.

9. The medical device according to claim 1, wherein the plurality of spines comprises three or more spines.

10. The medical device according to claim 1, wherein the plurality of spines comprises four or more spines.

11. The medical device according to claim 1, wherein the plurality of spines comprises five or more spines.

12. The medical device according to claim 1, wherein the flexible sheet comprises a plurality of distinct, separate sections, the sections having a unitary-like form in the deployed configuration.

13. The medical device according to claim 1, wherein the flexible sheet has a convex form in the deployed configuration.

14. The medical device according to claim 1, wherein the flexible sheet has a concave form in the deployed configuration.

15. The medical device according to claim 1, wherein the plurality of electrodes are used for treating the tissue.

16. A method for mapping tissue comprising the steps of:
    providing a device comprising a flexible elongated body; a handle connected to the elongated body; a plurality of spines connected to the elongated body; and a flexible sheet having a plurality of electrodes thereon, the flexible sheet and the plurality of electrodes defining a mapping assembly for mapping electrical information in tissue, wherein each spine is connected to a respective corner of the flexible sheet with the flexible sheet and the plurality of spines being movable from a collapsed configuration to a deployed configuration wherein the device further comprises a central spine shorter in length than the plurality of spines which is connected to the flexible sheet at a location near the center of the sheet;
    conforming the mapping assembly with the tissue when the device is in the deployed configuration;
    providing electrical information from the tissue using the plurality of electrodes; and
    forming a map with the electrical information.

17. The method according to claim 16, further comprising treating the tissue with the plurality of electrodes.

18. The method according to claim 16, further comprising providing location information of the central spine and the mapping assembly using at least one location sensor.

19. The method according to claim 18, further comprising providing location information in the form of six-dimensional coordinate information.

20. The method according to claim 18, further comprising providing mechanical information of the tissue.

21. The medical device according to claim 16, wherein the mapping assembly comprises a photoresist.

22. The medical device according to claim 21, wherein the photoresist comprises SU-8 material.

* * * * *